United States Patent
Lee et al.

(10) Patent No.: US 9,565,990 B2
(45) Date of Patent: Feb. 14, 2017

(54) ENDOSCOPE APPARATUS WITH SLAVE DEVICE AND MASTER DEVICE

(71) Applicants: Samsung Electronics Co., Ltd., Gyeonggi-do (KR); Industry-University Cooperation Foundation Hanyang University ERICA Campus, Gyeonggi-do (KR)

(72) Inventors: Yong-Hee Lee, Seoul (KR); Byung-Ju Yi, Gyeonggi-do (KR); Mun-Kue Park, Gyeonggi-do (KR); Jin-Won Lee, Gyeonggi-do (KR); Su-Kwang Lim, Seoul (KR); Jong-Tae Seo, Gyeonggi-do (KR); Jae-Hong Woo, Gyeonggi-do (KR)

(73) Assignees: Samsung Electronics Co., Ltd (KR); Industry-University Cooperation Foundation Hanyang University Erica Campus (KR)

( * ) Notice: Subject to any disclaimer, the term of this patent is extended or adjusted under 35 U.S.C. 154(b) by 463 days.

(21) Appl. No.: 14/168,365

(22) Filed: Jan. 30, 2014

(65) Prior Publication Data

US 2014/0296637 A1    Oct. 2, 2014

(30) Foreign Application Priority Data

Mar. 27, 2013    (KR) .................. 10-2013-0032697

(51) Int. Cl.
*A61B 1/04* (2006.01)
*A61B 1/00* (2006.01)
(Continued)

(52) U.S. Cl.
CPC ........... *A61B 1/00133* (2013.01); *A61B 34/30* (2016.02); *A61B 34/75* (2016.02); *A61M 25/01* (2013.01);
(Continued)

(58) Field of Classification Search
CPC ....... B25J 13/025; B25J 9/1633; B25J 9/1689; B25J 3/04; A61M 25/0113; G05B 2219/40144; G05B 2219/35419; G05B 2219/39439; G05B 2219/45117; G06F 3/016; G06F 19/3418; G06F 2203/015; G01L 5/226; Y10S 901/02; Y10S 901/15; A61B 17/00234; A61B 2017/003; A61B 2034/742; A61B 34/75; A61B 34/76; A61B 17/062; A61B 2034/2072; A61B 5/7475; A61B 34/30; A61B 2034/301; A61B 34/32; A61B 34/35; A61B 34/37
See application file for complete search history.

(56) References Cited

U.S. PATENT DOCUMENTS 5,766,016 A * 6/1998 Sinclair .................. G09B 23/28
                                                         340/407.1
6,096,004 A * 8/2000 Meglan .................. A61B 34/75
                                                         604/95.01

(Continued)

*Primary Examiner* — John P Leubecker
*Assistant Examiner* — Arnaldo Torres Diaz
(74) *Attorney, Agent, or Firm* — The Farrell Law Firm, P.C.

(57) ABSTRACT

An endoscope apparatus is provided. An endoscope apparatus includes a slave device including a plurality of drive motors configured to adjust insertion and insertion direction of an insertion tube of an endoscope, and a plurality of load sensors provided on the plurality of drive motors; and a master device including displacement sensors configured to generate signals for driving the drive motors according to an operator manipulation, and resistive motors configured to operate based on loads detected by the load sensors. The drive motors produce drive forces according to the signals generated by the displacement sensors and the resistive motors produce resistive forces corresponding to the operator manipulation based on the loads detected by the load sensors.

15 Claims, 5 Drawing Sheets

(51) Int. Cl.
*A61M 25/01* (2006.01)
*A61B 17/00* (2006.01)

(52) U.S. Cl.
CPC ........... *A61M 25/0113* (2013.01); *A61B 34/32* (2016.02); *A61B 34/35* (2016.02); *A61B 34/37* (2016.02); *A61B 34/76* (2016.02); *A61B 2017/003* (2013.01); *A61B 2034/301* (2016.02)

(56) References Cited

U.S. PATENT DOCUMENTS

| | | | | |
|---|---|---|---|---|
| 6,385,509 B2* | 5/2002 | Das | ........................ | B25J 9/1689 341/20 |
| 7,090,683 B2* | 8/2006 | Brock | .................... | A61B 90/36 606/1 |
| 7,880,717 B2* | 2/2011 | Berkley | .................. | G06F 3/016 318/560 |
| 8,005,571 B2* | 8/2011 | Sutherland | ............. | A61B 19/22 318/568.11 |
| 8,672,880 B2* | 3/2014 | Cohen | ............... | A61M 25/0105 600/114 |
| 8,684,952 B2* | 4/2014 | Weitzner | ............ | A61M 25/0113 600/585 |
| 8,755,864 B2* | 6/2014 | Hauck | .................. | A61B 5/6885 600/424 |
| 8,801,710 B2* | 8/2014 | Ullrich | ............... | A61B 18/1445 606/45 |
| 8,864,752 B2* | 10/2014 | Diolaiti | .................. | G05B 19/19 606/1 |
| 9,002,518 B2* | 4/2015 | Manzo | ............... | A61B 1/00149 700/245 |
| 9,205,227 B2* | 12/2015 | Cohen | ............... | A61M 25/0105 |
| 9,211,160 B2* | 12/2015 | Pivotto | .............. | A61B 19/2203 |
| 2001/0016804 A1* | 8/2001 | Cunningham | ....... | G09B 23/285 703/7 |
| 2002/0177843 A1* | 11/2002 | Anderson | ........ | A61B 17/32006 606/1 |
| 2003/0004610 A1* | 1/2003 | Niemeyer | ............ | A61B 34/70 700/245 |
| 2003/0005786 A1* | 1/2003 | Stuart | .................. | B23Q 1/5462 74/479.01 |
| 2003/0045888 A1* | 3/2003 | Brock | ........................ | B25J 3/04 606/130 |
| 2004/0183777 A1* | 9/2004 | Bevirt | ..................... | G05G 9/04 345/156 |
| 2005/0277096 A1* | 12/2005 | Hendrickson | ........ | G09B 23/285 434/262 |
| 2006/0106369 A1* | 5/2006 | Desai | ..................... | A61B 19/22 606/1 |
| 2007/0043338 A1* | 2/2007 | Moll | ............... | A61B 17/062 606/1 |
| 2007/0185404 A1* | 8/2007 | Hauck | .................. | A61B 5/6885 600/509 |
| 2008/0046122 A1* | 2/2008 | Manzo | ............... | A61B 1/00149 700/245 |
| 2008/0242929 A1 | 10/2008 | Ito | | |
| 2009/0012533 A1* | 1/2009 | Barbagli | ............. | G06F 19/3406 606/130 |
| 2010/0047753 A1* | 2/2010 | Feygin | ................. | G09B 23/285 434/272 |
| 2010/0168918 A1* | 7/2010 | Zhao | ................. | B25J 9/1689 700/259 |
| 2011/0028894 A1* | 2/2011 | Foley | ................. | A61M 25/0136 604/95.01 |
| 2011/0077777 A1* | 3/2011 | Yi | ........................... | B25J 9/1679 700/264 |
| 2011/0166513 A1* | 7/2011 | Cohen | ............... | A61M 25/0105 604/95.01 |
| 2012/0053701 A1* | 3/2012 | Yi | ........................... | B25J 9/0048 700/3 |
| 2012/0179169 A1* | 7/2012 | Swarup | ............... | A61B 19/2203 606/130 |
| 2012/0197082 A1 | 8/2012 | Uchiyama et al. | | |
| 2012/0245595 A1* | 9/2012 | Kesavadas | ............. | B25J 9/1689 606/130 |
| 2012/0290134 A1* | 11/2012 | Zhao | ............ | B25J 9/1697 700/259 |
| 2013/0006268 A1* | 1/2013 | Swarup | .................. | A61B 34/37 606/130 |
| 2013/0197697 A1* | 8/2013 | Schaible | ............ | A61B 19/2203 700/260 |
| 2013/0226197 A1* | 8/2013 | Diolaiti | .................. | G05B 19/19 606/130 |
| 2014/0195010 A1* | 7/2014 | Beira | ............... | A61B 17/00234 700/3 |
| 2015/0112486 A1* | 4/2015 | Larkin | .................... | G01L 5/226 700/258 |
| 2015/0128763 A1* | 5/2015 | Yoon | ..................... | F16H 37/065 74/665 A |

* cited by examiner

ENDOSCOPE APPARATUS WITH SLAVE DEVICE AND MASTER DEVICE

PRIORITY

This application claims priority under 35 U.S.C. §119(a) to a Korean Patent Application filed in the Korean Intellectual Property Office on Mar. 27, 2013 and assigned Serial No. 10-2013-0032697, the entire disclosure of which is incorporated herein by reference.

BACKGROUND OF THE INVENTION

1. Field of the Invention

The present invention generally relates to medical equipment, and more particularly, to a medical endoscope apparatus.

2. Description of the Related Art

A medical endoscope directly captures images of organs of patients, enabling early diagnosis of lesions and even surgical operations, such as removal of lesions.

For cultivating endoscopy operators, training using simulation devices is preceded, and in use of a real endoscope apparatus, a simulation device is also used. For example, an endoscope apparatus has been commonly used, which includes a master device manipulated by an operator and a slave device that directly drives an insertion tube of the endoscope apparatus according to the operator's manipulation. When using endoscope apparatuses, an insertion time varies with the skill of each operator; and a technique for making an insertion time or an insertion speed uniform is needed for operating on a patient who receives an endoscopic operation. Moreover, an operator directly moves an endoscope by both hands and uses the master device for clear visibility. At this time, to manipulate the master device, a technique for reducing the fatigue of the operator is required.

Such endoscope apparatuses are disclosed in U.S. Patent Publication No. 2012/0197082 A1, which published on Aug. 2, 2012 (hereinafter, referred to as a "first document") and U.S. Patent Publication No. 2008/0242929 A1, which published on Oct. 2, 2008 (hereinafter, referred to as a "second document"). An endoscope apparatus disclosed in the first document discloses an insertion structure of a vibration type in which the operator applies an insertion drive signal using a foot switch, and an insertion tube having a spiral casing advances (or moves forward) while rotating. An endoscope apparatus disclosed in the second document discloses a structure in which application of a drive signal for movement of an endoscope, such as insertion or bending, and control of an auxiliary device, such as cleaning/suction, are performed by one controller.

However, in the endoscope apparatus disclosed in the first document, the insertion tube simultaneously advances and rotates inside an organ, and thus when contacting an inner wall of the organ, the insertion tube may cause twisting of the organ. Moreover, the endoscope apparatus disclosed in the first document uses a knob structure in a general endoscope, resulting in some limitations in solving the operator fatigue issue. The endoscope apparatus disclosed in the second document may control operations of the endoscope and the auxiliary device by one controller, but during advancing of the insertion tube, damage such as twisting of an organ may be caused. In addition, there is no way for the operator to know a reaction force corresponding to the twisting of the organ or a resistance of the inner wall of the organ during insertion of the insertion tube, further increasing a risk of damage to the organ.

SUMMARY OF THE INVENTION

The present invention has been made to address at least the problems and disadvantages described above and to provide at least the advantages described below.

Accordingly, an aspect of the present invention is to provide an endoscope apparatus that addresses fatigue of an operator.

Another aspect of the present invention is to provide an endoscope apparatus that allows an operator to recognize a reaction force corresponding to twisting of an organ or a resistance of an inner wall of the organ during insertion of an insertion tube.

In accordance with an aspect of the present invention, an endoscope apparatus is provided, which includes a slave device including a plurality of drive motors configured to adjust insertion and insertion direction of an insertion tube of an endoscope and a plurality of load sensors provided on the plurality of drive motors; and a master device including displacement sensors configured to generate signals for driving the drive motors according to an operator's manipulation and resistive motors configured to operate based on loads detected by the load sensors. The drive motors produce drive forces according to the signals generated by the displacement sensors and the resistive motors produce resistive forces corresponding to the operator manipulation based on the loads detected by the load sensors.

BRIEF DESCRIPTION OF THE DRAWINGS

The above and other aspects, features, and advantages of various embodiments of the present invention will be more apparent from the following detailed description taken in conjunction with the accompanying drawings, in which.

Throughout the drawings, like reference numerals will be understood to refer to like parts, components, and structures.

DETAILED DESCRIPTION OF EMBODIMENTS OF THE PRESENT INVENTION

Hereinafter, various embodiments of the present invention will be described with reference to the accompanying drawings. Other aspects, advantages, and salient features of the present invention will become apparent to those skilled in the art from the following detailed description, which, taken in conjunction with the annexed drawings, discloses various embodiments of the present invention. In the following description of the present invention, a detailed description of known functions and configurations incorporated herein will be omitted for clarity.

Figure 1:
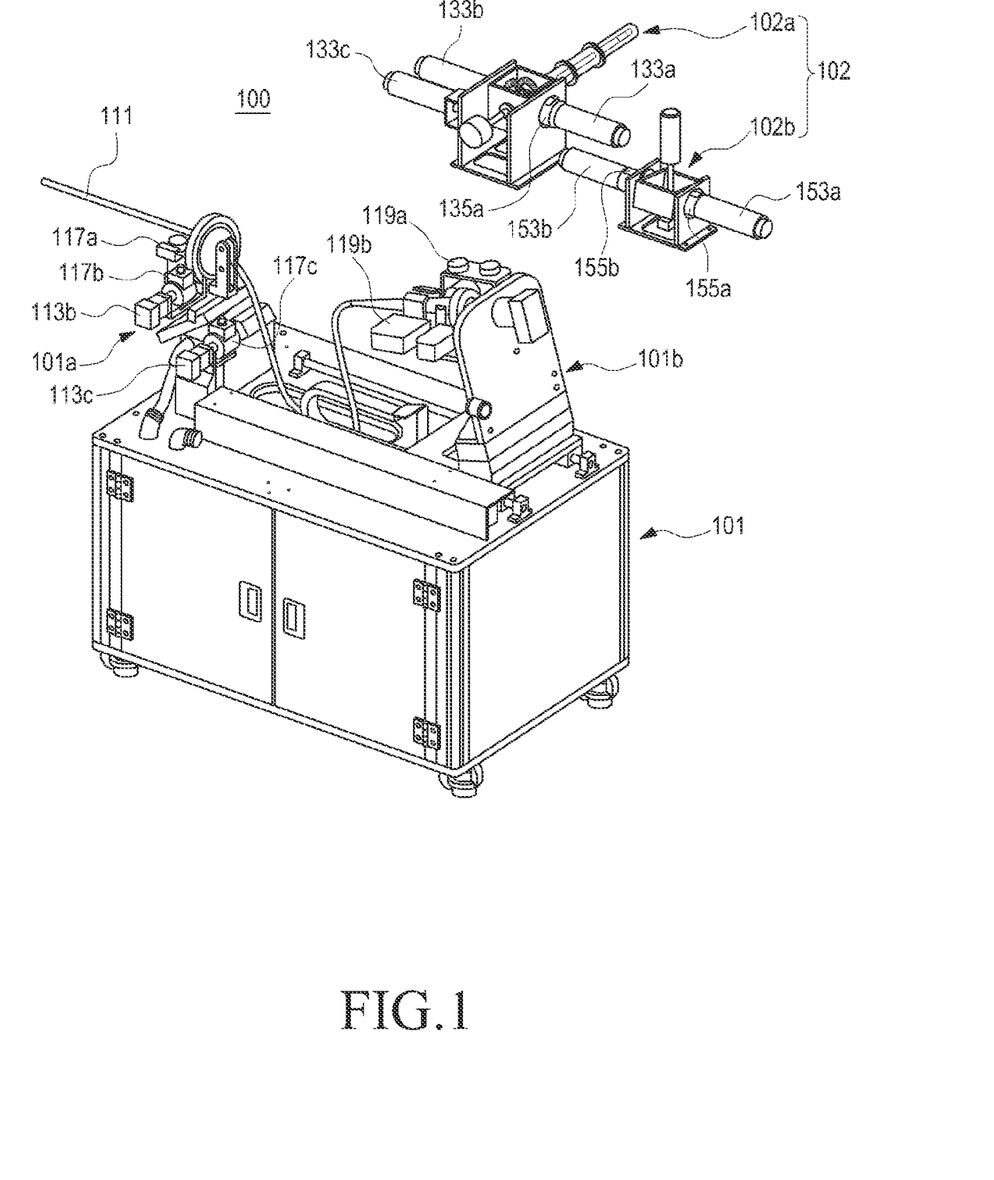
FIG. 1 illustrates an endoscope apparatus according to an embodiment of the present invention.
Figure 5:
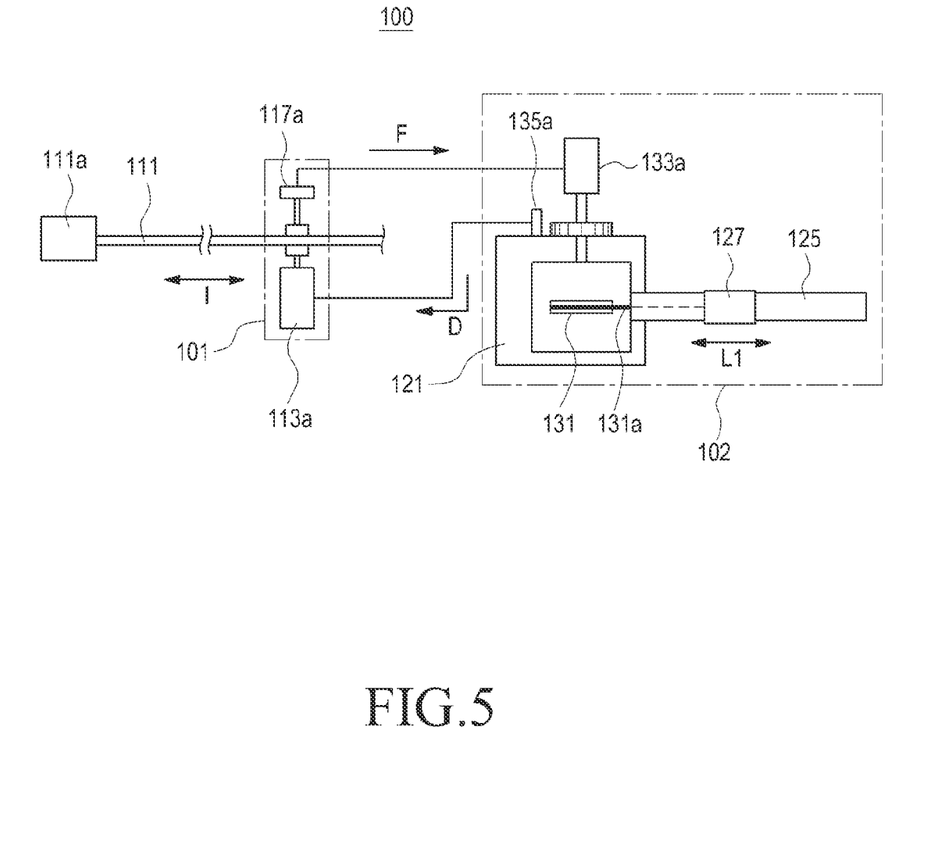
FIG. 5 is a schematic diagram illustrating an operation of an endoscope apparatus shown in FIG. 1 according to an embodiment of the present invention.

Referring to FIGS. 1 and 5, an endoscope apparatus 100 according to an embodiment of the present invention includes a slave device 101 that inserts an insertion tube 111 of an endoscope into an organ of a patient and adjusts an insertion direction during insertion and a master device 102 that generates a drive signal according to an operator's manipulation. The slave device 101 includes a plurality of drive motors 113a, 113b, 113c, 115a, and 115b, each of which operates according to a drive signal generated from the master device 102 to produce a drive force for insertion of the insertion tube 111 and adjustment of insertion direction and orientation of the insertion tube 111. The slave device 101 includes load sensors 117a, 117b, 117c, 119a, and 119b to detect a load, that is, a reaction force, produced during insertion, and the master device 102 includes resistive motors 133a, 133b, 133c, 153a, and 153b to produce resistive forces corresponding to the operator's manipulation based on reaction forces detected from the load sensors 117a, 117b, 117c, 119a, and 119b. The master device 102 includes displacement sensors 135a, 135b, 135c, 155a, and 155b, for example, encoders, that detect the operator's manipulation to generate a drive signal for driving the drive motors 113a, 113b, 113c, 115a, and 115b.

Figure 2:
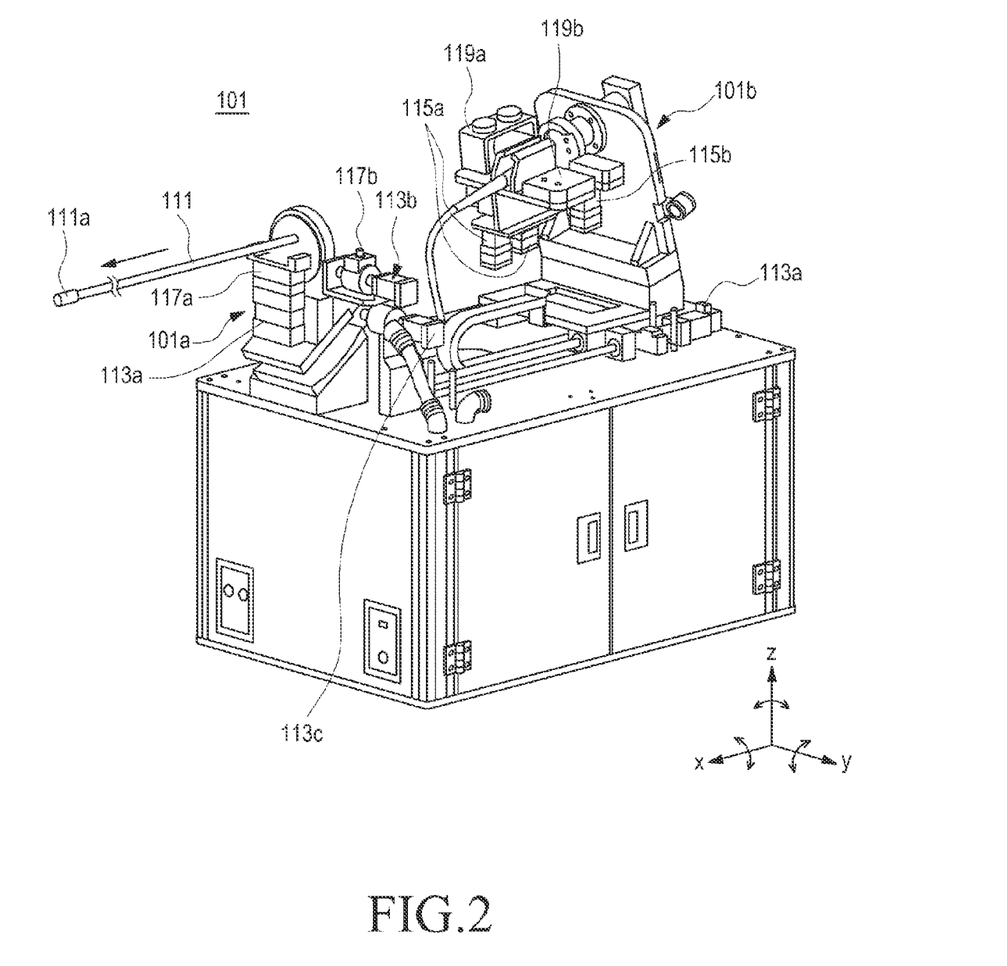
FIG. 2 illustrates a slave device of an endoscope apparatus shown in FIG. 1 according to an embodiment of the present invention.

The slave device 101 includes an insertion drive slave device 101a for insertion and direction adjustment of the insertion tube 111 and a rotation drive slave device 101b for adjustment of an orientation of a front end portion (shown as 111a in FIG. 5) of the insertion tube 111, for example, for adjustment of a capturing direction. The drive motors 113a, 113b, 113c, 115a, and 115b are mounted on the insertion drive slave device 101a and the rotation drive slave device 101b, respectively.

Drive motors mounted on the insertion drive slave device 101a include a first drive motor 113a for providing an insertion drive force along the insertion direction of the insertion tube 111, a second drive motor 113b for providing a roll drive force that causes twisting of the insertion tube 111 with respect to the moving direction of the insertion tube 111, and a third drive motor 113c for providing a pitch drive force that causes bending of the insertion tube 111 with respect to the moving direction of the insertion tube 111. The first drive motor 113a produces an insertion drive force for advancing (moving forward) or retreating (moving backward) the insertion tube 111 along the insertion direction. The moving direction of the insertion tube 111 corresponding to an operation of the first drive motor 113a is defined as an x-axis. As the second drive motor 113b operates, the insertion tube 111 rotates around the x-axis. For convenience of a description, the x-axis is shown in the form of a straight line, but the insertion tube 111 is bent in various forms when inserted into an organ of a patient. Thus, the x-axis mentioned in the detailed description may also be deformed by bending of the insertion tube 111. That is, it may be clearer to define the x-axis as the lengthwise direction of the insertion tube 111. As the third drive motor 113c operates, the insertion tube 111 is deformed to be bent with respect to its moving direction. Deformation of the insertion tube 111 corresponding to the operation of the third drive motor 113c will be generally in a pitch direction, that is, deformation in an up/down direction along the moving direction of the insertion tube 111. However, the moving direction of the insertion tube 111 is adjusted by the second drive motor 113b and the third drive motor 113c at the same time, such that as the second drive motor 113b and the third drive motor 113c operate simultaneously, the moving direction of the insertion tube 111 may be adjusted in a yaw direction, that is, a left/right direction.

The rotation drive slave device 101b adjusts the orientation of the front end portion 111a of the insertion end 111, and is generally used to adjust a capturing direction. To adjust the orientation of the front end portion 111a of the insertion tube 111, drive motors mounted on the rotation drive slave device 101b include a plurality of fourth drive motors 115a. The fourth drive motors 115a produce drive forces for adjusting the orientation of the front end portion 111a of the insertion tube 111 in the pitch direction or the yaw direction, independently of the first through third drive motors 113a, 113b, and 113c. In the following description, adjustment in the pitch direction may be referred as to "rotation around the y-axis and adjustment in the yaw direction may be referred as to rotation around the z-axis. If the insertion tube 111 connected to the endoscope apparatus 100 includes a tool for a surgical operation, the fifth drive motors 115b for adjustment of the moving direction of the tool may be mounted on the rotation drive slave device 101b.

The load sensors 117a, 117b, 117c, 119a, and 119b sense a reaction force produced in the insertion tube 111 with respect to the drive forces of the drive motors 113a, 113b, 113c, 115a, and 115b. That is, the load sensors 117a, 117b, 117c, 119a, and 119b detect resistive forces produced when the insertion tube 111 advances or the moving direction of the insertion tube 111 is not changed according to driving of the drive motors 113a, 113b, 113c, 115a, and 115b. The load sensors 117a, 117b, 117c, 119a, and 119b may use torque sensors. In other words, the torque sensors are connected to drive shafts of the drive motors 113a, 113b, 113c, 115a, and 115b to be used as the load sensors 117a, 117b, 117c, 119a, and 119c. The resistive motors 133a, 133b, 133c, 153a, and 153b mounted on the master device 102 produce resistive forces corresponding to operator's manipulation based on reaction forces detected from the load sensors 117a, 117b, 117c, 119a, and 119b.

Figure 3:
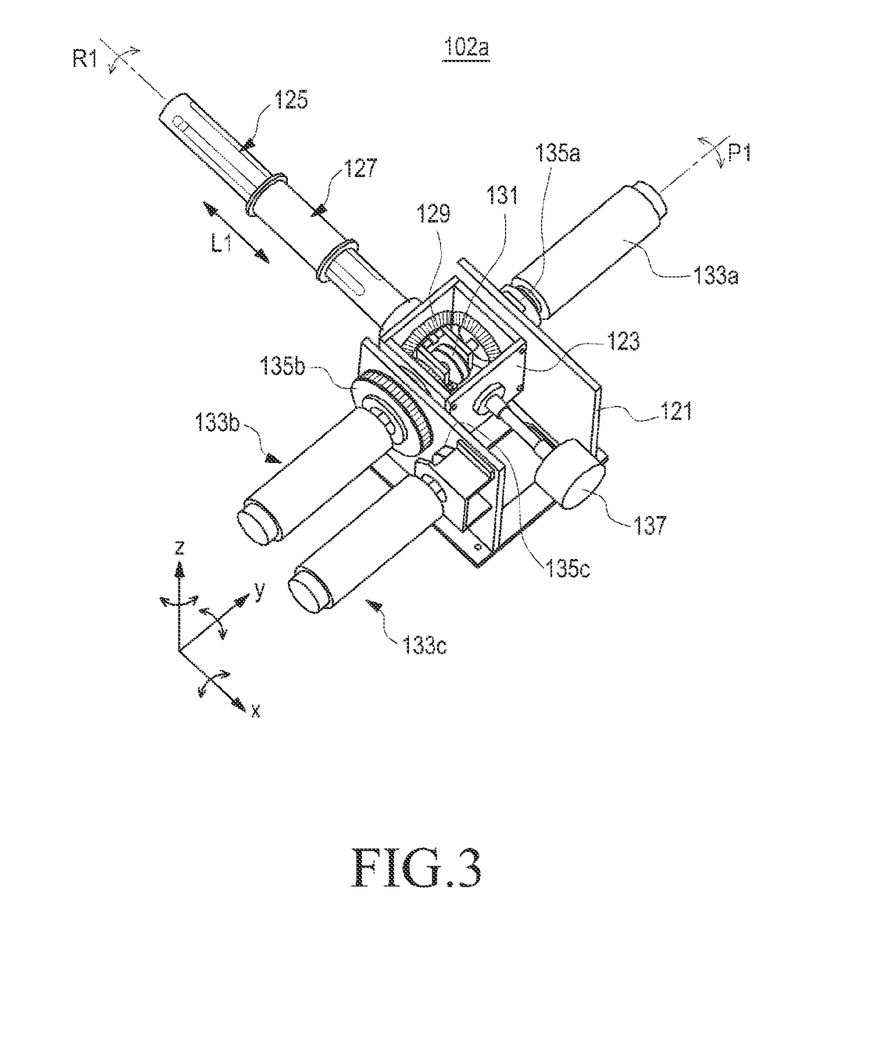
FIG. 3 illustrates an insertion drive master device of a master device of an endoscope apparatus shown in FIG. 1 according to an embodiment of the present invention.
Figure 4:
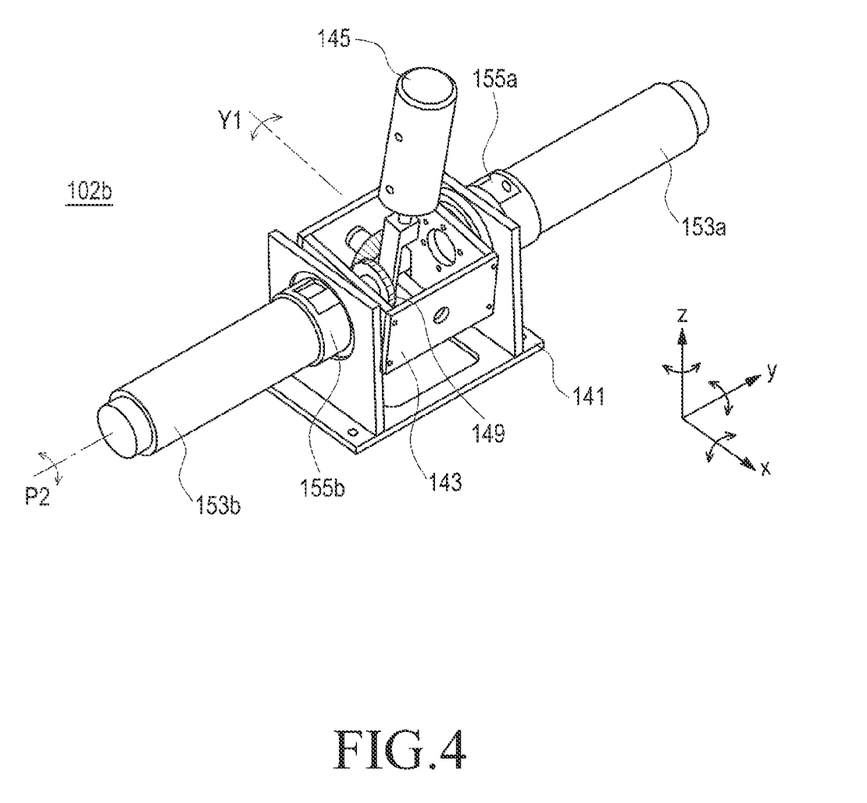
FIG. 4 illustrates a rotation drive master device of a master device of an endoscope apparatus shown in FIG. 1 according to an embodiment of the present invention.

Referring to FIGS. 3 and 4, the master device 102 may include an insertion drive master device 102a and a rotation drive master device 102b. The master device 102 is directly manipulated by the operator to generate a drive signal for the drive motors 113a, 113b, 113c, 115a, and 115b according to the operator's manipulation, and provide a resistive force corresponding to the operator's manipulation based on the reaction forces sensed by the load sensors 117a, 117b, 117c, 119a, and 119b.

The insertion drive master device 102a generates an insertion drive signal for inserting the insertion tube 111, a roll drive signal for twisting the insertion tube 111, and a pitch drive signal for bending the insertion tube 111. That is, the insertion drive master device 102a substantially generates signals for driving the insertion drive slave device 101a. If the insertion tube 111 connected to the endoscope apparatus 100 includes a tool for a surgical operation, the drive signal for the fifth drive motors 115b may be generated according to driving of the insertion drive master device 102a. The rotation drive master device 102b generates a second pitch drive signal and a yaw drive signal for adjusting the orientation of the front end portion 111a of the insertion tube 111. In other words, the rotation drive master device 102b generates signals for driving the rotation drive slave device 101b.

Referring to FIG. 3, the insertion drive master device 102a includes a fixing bracket 121, a rotation bracket 123, a guide rail 125, and a slider 127. The fixing bracket 121 fixes the insertion drive master device 102a at a predetermined position and provides a space for mounting the rotation bracket 123 and so forth. The rotation bracket 123 is coupled to the fixing bracket 121 to rotate around a first rotation axis y. A drive signal for causing bending deformation of the insertion tube 111 during insertion of the insertion tube 111, that is, a pitch drive signal P1 is generated from rotation of the rotation bracket 123.

The guide rail 125 extends from the rotation bracket 123 along a second rotation axis x. Herein, the second rotation axis x is oriented perpendicular to the first rotation axis y. As the guide rail 125 extends from the rotation bracket 123, the guide rail 125 pivots with respect to the first rotation axis y. Thus, the operator moves the guide rail 125 to rotate the rotation bracket 123 with respect to the fixing bracket 121, and as mentioned above, when the rotation bracket 123 rotates, the pitch drive signal P1 is generated.

The slider 127 is coupled to the guide rail 125 to linearly reciprocates in the extending direction of the guide rail 125, that is, along the second rotation axis x. The slider 127 also rotates around the second rotation axis x on the guide rail 125. As the slider 127 linearly reciprocates, an insertion drive signal L1 for advancing or retreating the insertion tube 111 is generated, and as the slider 127 rotates, a roll drive signal R1 for twisting the insertion tube 111 is generated. The insertion drive master device 102*a* generates drive signals for advancing or retreating the insertion tube 111 or adjusting the moving direction of the insertion tube 111. The drive signals are generated by the aforementioned displacement sensors.

Some of the plurality of displacement sensors, for example, the displacement sensors 135*a*, 135*b*, and 135*c* are provided to the fixing bracket 121 to detect rotation of the rotation bracket 123 and linear reciprocation and rotation of the slider 127. A gear assembly 129 including a plurality of gears is mounted in the rotation bracket 123. The gears of the gear assembly 129 may be mounted such that they rotate independently to each other or some of them rotate in association with each other. The displacement sensors 135*a*, 135*b*, and 135*c* mounted in the fixing bracket 121 may include optical or mechanical encoders combined with the gears of the gear assembly 129. Meanwhile, the gear assembly 129 may include a pulley 131 and a wire (shown as 131*a* in FIG. 5) to convert linear movement of the slider 127 into rotation. The wire 131*a* may be replaced with a timing belt.

The displacement sensor for detecting a linear movement distance of the slider 127 may include an optical or mechanical encoder that uses the pulley 131. Rotation of the slider 127 or rotation of the rotation bracket 123 may be connected to the rotation of one of the gears of the gear assembly 129, and the displacement sensors 135*a*, 135*b*, and 135*c* detect the amount of rotation of the gear connected to rotation of the slider 127 or rotation of the rotation bracket 123 to generate the roll drive signal R1 or the pitch drive signal P1.

According to the drive signals generated from the insertion drive master device 102*a*, the drive motors mounted on the insertion drive slave device 101*a*, that is, the first through third drive motors 113*a*, 113*b*, and 113*c*, operate to adjust insertion and insertion direction of the insertion tube 111. Consequently, at least three displacement sensors 135*a*, 135*b*, and 135*c* are mounted in the fixing bracket 121, such that the first displacement sensor detects a linear movement of the slider 127, the second displacement sensor detects the amount of rotation of the slider 127, and the third displacement sensor detects the amount of rotation of the rotation bracket 123 to generate the insertion drive signal L1, the roll drive signal R1, and the pitch drive signal P1, respectively.

An operation switch may be installed in the slider 123. When the operator manipulates the operation switch to adjust insertion of the insertion tube 111, the insertion drive master device 102*a* may generate a drive signal. For example, according to the manipulated operation switch, the insertion drive master device 102*a* may switch to an operation mode or a standby mode. The insertion drive master device 102*a* may be set to the operation mode when the operation switch is pressed.

The rotation bracket 123 may be further provided with a balance weight 137. Because the guide rail 125 extends to a side from the rotation bracket 123 along the first rotation axis y, the operator has to manipulate the slider 127 while bearing the weights of the guide rail 125 and the slider 127. Thus, by using the balance weight 137 mounted in the rotation bracket 123, the operator's load may be eased. If the guide rail 125 extends from an outer circumferential surface of one side of the rotation bracket 123, the balance weight 137 extends from an outer circumferential surface of the other side of the rotation bracket 123 along the second rotation axis x. That is, the guide rail 125 and the balance weight 137 extend from the rotation bracket 123 in a direction away from each other. Thus, the guide rail 125 and the slider 127 are generally weight-balanced with the balance weight 137 with respect to the first rotation axis y. In this way, the operator who manipulates the slider 125 does not need to bear the weights of the guide rail 125 and the slider 127, thus, the operator's fatigue in the endoscopy operation may be reduced.

The resistive motors 133*a*, 133*b*, and 133*c* provided in the insertion drive master device 102*a* are mounted on a gear or displacement sensor corresponded to rotation of the rotation bracket 123, a gear, pulley, or displacement sensor corresponded to linear movement of the slider 127, and a gear or displacement sensor corresponded to rotation of the slider 127, respectively. That is, at least three resistive motors 133*a*, 133*b*, and 133*c* may be mounted on the insertion drive master device 102*a*, and a gear or pulley corresponded to movement of the slider 127 or the rotation bracket 123 may be connected to or mounted on the driving shafts of the resistive motors 133*a*, 133*b*, and 133*c*.

The resistive motors 133*a*, 133*b*, and 133*c* produce resistive forces corresponding to operator's manipulation based on the reaction forces sensed by the load sensors 117*a*, 117*b*, and 117*c*, respectively, to suppress movement of the rotation bracket 123 or the slider 127. The operator may also exert a larger force according to the resistive forces produced by the resistive motors 133*a*, 133*b*, and 133*c* to move the rotation bracket 123 or the slider 127. However, these resistive forces simulate interference caused by the inner wall of an organ or the like during insertion, and the operator may recognize interference between the insertion tube 111 and the inner wall of the organ from the resistive forces. Once recognizing the resistive forces during manipulation of the insertion drive master device 102*a*, the operator may temporarily retreat the insertion tube 111 or change the insertion direction of the insertion tube 111 in order to smoothly insert the insertion tube 111 and thus alleviate the pain of the patient.

Referring to FIG. 4, the rotation drive master device 102*b* includes a second fixing bracket 141, a second rotation bracket 143, and an adjustment grip 145. The second fixing bracket 141 fixes the rotation drive master device 102*b* at a predetermined position, and provides a space for mounting the second rotation bracket 143. The second rotation bracket 143 is coupled to the second fixing bracket 141 to rotate around the y-axis. Rotation of the second rotation bracket 143 generates a second pitch drive signal P2 in the advancing direction of the insertion tube 111. That is, the operator rotates the second rotation bracket 143 to adjust the orientation of the insertion tube 111 in the up/down direction.

However, it should be noted that the insertion tube 111 is also driven in a roll direction, and thus, rotation of the second rotation bracket 143 does not necessarily adjust the orientation of the front end portion 111a of the insertion tube 111 in the pitch direction.

The adjustment grip 145 is coupled to the second rotation bracket 143 to pivot with respect to the y-axis together with the second rotation bracket 143 and to rotate around the z-axis with respect to the second rotation bracket 143. The z-axis rotation of the adjustment grip 145 generates a yaw drive signal Y1 with respect to the advancing direction of the insertion tube 111. In other words, by rotating the adjustment grip 145 around the z-axis, the operator may adjust the orientation of the insertion tube 111 in the left/right direction.

At least one or two or more displacement sensors 155a and 155b may be mounted in the rotation drive master device 102b to detect the amount of rotation or the amount of pivoting of the second rotation bracket 143 and the adjustment grip 145. The displacement sensor 155a for detecting the amount of rotation of the second rotation bracket 143 is mounted on the second fixing bracket 141 in the y-axis. In this case, a first resistive motor 153a connected to one of the load sensors mounted on the load drive slave device 101b is mounted on the rotation drive master device 102b. A drive shaft of the first resistive motor 153a is used as a support shaft for rotation of the second rotation bracket 143. Thus, at least one of the displacement sensors 155a and 155b may be mounted on the drive shaft of the first resistive motor 153a to detect the amount of rotation of the second rotation bracket 143. If a separate signal is not provided by the load sensor, the first resistive motor 153a does not operate and the operator may freely rotate the second rotation bracket 143.

The displacement sensor 155b for detecting the amount of pivoting of the adjustment grip 145 may be mounted on the second rotation bracket 143. In addition, the second resistive motor 153b that produces a resistive force with respect to pivoting of the adjustment grip 145 in the z-axis may also be mounted on the second bracket 143. However, as an example, the second resistive motor 153b is mounted on the second fixing bracket 141, and the second resistive motor 153b may be associated with pivoting of the adjustment grip 145 through a second gear assembly 149 installed in the second rotation bracket 143.

The displacement sensor 155b that detects the amount of pivoting of the adjustment grip 145 in the z-axis may be mounted on one of gears of the second gear assembly 149 or on the drive shaft of the second resistive motor 153b. That is, the amount of pivoting of the adjustment grip 145 may be detected from the amount of rotation of one of the gears of the second gear assembly 149 or the amount of rotation of the drive shaft of the second resistive motor 153b. One of the displacement sensors 155a and 155b mounted on the second fixing bracket 141 detects the amount of pivoting of the adjustment grip 1145 to generate the yaw drive signal Y1 in the advancing direction of the insertion tube 111.

The second resistive motor 153b is also connected to one of the load sensors mounted on the rotation drive slave device 101b. If a separate signal is not provided by the connected load sensor of the rotation drive slave device 101b, the second resistive motor 153b does not operate and the operator may freely pivot the adjustment grip 145.

A separate operation switch may be installed in the adjustment grip 145. When the operator manipulates the operation switch to adjust the orientation of the insertion tube 111, the rotation drive master device 102b may generate a drive signal. For example, according to the manipulated operation switch, the rotation drive master device 102b may switch to an operation mode or a standby mode. The rotation drive master device 102b may be set to the operation mode when the operation switch is pressed.

FIG. 5 is a diagram schematically illustrating the slave device 101 and the master device 102 to describe the operation of the endoscope apparatus 100.

Referring to FIG. 5, insertion of the insertion tube 111 will be described. Those of ordinary skill in the art may easily understand roll drive or pitch drive during insertion of the insertion tube 111 or pitch drive or yaw drive for adjustment orientation.

Referring to FIG. 5, the drive motor 113a for generating a drive force for insertion of the insertion tube 111 is provided in the slave device 101, and a roller and the load sensor 117a are mounted on the drive shaft of the drive motor 113a. While the roller rotates in direct contact with an outer circumferential surface of the insertion tube 111 according to the operation of the drive motor 113a, the insertion tube 111 advances or retreats along an insertion direction I. The fixing bracket 121, the rotation bracket 123, the guide rail 125, and the slider 127 are provided in the master device 102, and the pulley 131 and the wire 131a for converting linear movement of the slider 127 with respect to the guide rail 125 into rotation are mounted in the rotation bracket 123. The wire 131a may include a timing belt. The pulley 131 is connected to the resistive motor 133a through the drive shaft; and the encoder using the gear and a photo sensor on the drive shaft, that is, the displacement sensor 135a, is provided. The resistive motor 133a is connected to the load sensor 117a, and the drive motor 113a is connected to the displacement sensor 135a.

After the operator linearly moves the slider 127, the pulley 131 and the drive shaft rotate and the displacement sensor 135a detects the amount of rotation of the drive shaft and the amount of linear movement of the slider 127. If a separate operation switch is provided, detection of the amount of movement of the slider 127 is performed when the master device 102 is set to the operation mode according to the manipulated operation switch. The displacement sensor 135a generates an insertion drive signal D based on the amount of movement of the slider 127 and delivers the insertion drive signal D to the drive motor 113a. The drive motor 113a operates according to the insertion drive signal D to advance or retreat the insertion tube 111.

During insertion of insertion tube 111, if the inner wall of the organ interferes with the insertion tube 111 or the front end portion 111a of the insertion tube 111, a reaction force with respect to driving force produced by the driving motor 113a is generated and the load sensor 117a detects the reaction force. A torque required for advancing the insertion tube 111 in proportional to the input insertion drive signal D is detected by the load sensor 117a to calculate the reaction force during insertion. Once the reaction force is detected, the load sensor 117a generates a resistive force drive signal F and delivers the resistive force drive signal F to the resistive motor 133a which then produces a resistive force corresponding to the operator's manipulation. Due to the resistive force, the operator should exert a larger force to linearly move the slider 127 to recognize that the insertion tube 111 is interfered with the inner wall of the organ. Thus, the operator manipulates the master device 102, when necessary, to adjust the advancing direction of the insertion tube 111.

According to various embodiments of the present invention, the load sensor provided in the slave device senses a reaction force produced in the insertion tube; and the resistive motor provided on the master device operates based on the reaction force sensed by the load sensor to produce a resistive force corresponding to operator's manipulation, thereby simulating real insertion of the insertion tube. Hence, the operator recognizes interference between the insertion tube and the inner wall of the organ and adjusts the moving direction of the insertion tube, thus, to avoid interference between the insertion tube and the inner wall of the organ. Moreover, the insertion drive signal is applied using the slider; and the rotation drive signal is applied using the adjustment grip having a joystick structure. Also, by using the balance weight, the fatigue of the operator is reduced, thereby providing a comfortable operation environment to the operator. Furthermore, the master device simulates real insertion of the insertion tube, thus shortening the time for the operator to master the operation and reducing skill differences among operators. Therefore, uniform operation time and insertion speed may be provided to patients.

While the present invention has been particularly shown and described with reference to certain embodiments thereof, various changes in form and detail may be made therein without departing from the spirit and scope of the present invention as defined by the following claims. Accordingly, the scope of the present invention will be defined by the appended claims and equivalents thereto.

What is claimed is:

1. An endoscope apparatus comprising:
    a slave device including a plurality of drive motors configured to adjust insertion and insertion direction of an insertion tube of an endoscope, and a plurality of load sensors configured on the plurality of drive motors; and
    a master device including displacement sensors configured to generate signals for driving the drive motors according to an operator manipulation, and resistive motors configured to operate based on loads detected by the load sensors,
    wherein the drive motors produce drive forces according to the signals generated by the displacement sensors and the resistive motors produce resistive forces corresponding to the operator manipulation based on the loads detected by the load sensors, and
    wherein the slave device further comprises:
        an insertion drive slave device configured to produce an insertion drive force causing linear movement of the insertion tube, a roll drive force causing twisting of the insertion tube with respect to the insertion direction of the insertion tube, and a pitch drive force bending the insertion tube with respect to the insertion direction of the insertion tube; and
        a rotation drive slave device configured to produce a second pitch drive force and a yaw drive force for adjusting an orientation of a front end portion of the insertion tube.

2. The endoscope apparatus of claim 1, wherein the load sensors comprise torque sensors.

3. The endoscope apparatus of claim 1, wherein the load sensors sense a reaction force produced in the insertion tube with respect to the drive forces produced by the drive motors.

4. The endoscope apparatus of claim 1, wherein the master device further comprises:
    an insertion drive master device configured to generate an insertion drive signal for inserting the insertion tube, a roll drive signal for twisting the insertion tube with respect to the insertion direction of the insertion tube, and a pitch drive signal for bending the insertion tube with respect to the insertion direction of the insertion tube; and
    a rotation drive master device configured to generate a second pitch drive signal and a yaw drive signal for adjusting an orientation of a front end portion of the insertion tube.

5. The endoscope apparatus of claim 4, wherein the insertion drive slave device operates according to drive signals generated by the insertion drive master device, and
    wherein the rotation drive slave device operates according to drive signals generated by the rotation drive master device.

6. The endoscope apparatus of claim 4, wherein the insertion drive master device comprises:
    a fixing bracket;
    a rotation bracket coupled to the fixing bracket, configured to rotate around a first rotation axis;
    a guide rail extending from the rotation bracket along a second rotation axis that is perpendicular to the first rotation axis; and
    a slider coupled to the guide rail, configured to rotate around the second rotation axis and to linearly move along the second rotation axis.

7. The endoscope apparatus of claim 6, wherein a plurality of the displacement sensors are provided in the fixing bracket, and
    among the plurality of displacement sensors provided in the fixing bracket, a first displacement sensor detects linear movement of the slider to generate an insertion drive signal, a second displacement sensor detects rotation of the slider around the second rotation axis to generate a roll drive signal, and a third displacement sensor detects rotation of the rotation bracket around the first rotation axis to generate a pitch drive signal.

8. The endoscope apparatus of claim 6, wherein the insertion drive master device further comprises:
    a gear assembly configured in the rotation bracket, and
    a plurality of resistive motors configured in the fixing bracket,
    wherein the gear assembly delivers resistive forces produced from the resistive motors to the slider and the rotation bracket.

9. The endoscope apparatus of claim 8, wherein the gear assembly comprises a pulley that operates in association with linear movement of the slider.

10. The endoscope apparatus of claim 8, wherein the displacement sensors detect a rotation displacement of at least one of gears of the gear assembly to detect a displacement of the slider or the rotation bracket.

11. The endoscope apparatus of claim 6, wherein the insertion drive master device further comprises:
    a balance weight extending from the rotation bracket along the second rotation axis,
    wherein the guide rail and the balance weight extend from an outer circumferential surface of a first side of the rotation bracket and from an outer circumferential surface of a second side of the rotation bracket in a direction away from each other, respectively.

12. The endoscope apparatus of claim 4, wherein the rotation drive master device comprises:
    a second fixing bracket;
    a second rotation bracket coupled to the second fixing bracket, configured to rotate; and
    an adjustment grip coupled to the second rotation fixing bracket, configured to pivot, wherein the adjustment grip pivots with respect to a rotation axis that is perpendicular to a rotation axis of the second rotation bracket, rotation of the second rotation bracket generates the second pitch drive signal, and pivoting of the adjustment grip generates the yaw drive signal.

13. The endoscope apparatus of claim 12, wherein the rotation drive master device comprises:

displacement sensors mounted on the second fixing bracket; and resistive motors mounted on the second fixing bracket, wherein one of the displacement sensors mounted on the second fixing bracket detects a displacement of the second rotation bracket with respect to the second fixing bracket, and another one of the displacement sensors mounted on the second fixing bracket detects a displacement of the adjustment grip with respect to the second rotation bracket, and wherein the resistive force produced from one of the resistive motors mounted on the second fixing bracket acts on rotation of the second rotation bracket and the resistive force produced from another one of the resistive motors mounted on the second fixing bracket acts on pivoting of the adjustment grip.

14. The endoscope apparatus of claim 13, wherein the rotation drive master device further comprises:

a gear assembly mounted in the second rotation bracket, wherein the gear assembly delivers the resistive force produced from another one of the resistive motors mounted on the second fixing bracket to the adjustment grip.

15. The endoscope apparatus of claim 14, wherein the displacement of the adjustment grip is detected based on a displacement of one of gears of the gear assembly.

* * * * *